(12) United States Patent
Thrush et al.

(10) Patent No.: US 7,705,990 B2
(45) Date of Patent: Apr. 27, 2010

(54) OPTICAL SOURCES FOR SPR APPLICATIONS

(75) Inventors: Evan P. Thrush, San Francisco, CA (US); Gregory D. VanWiggeren, San Jose, CA (US); Douglas M Baney, Los Altos, CA (US)

(73) Assignee: Agilent Technologies, Inc., Santa Clara, CA (US)

(*) Notice: Subject to any disclaimer, the term of this patent is extended or adjusted under 35 U.S.C. 154(b) by 763 days.

(21) Appl. No.: 11/462,681

(22) Filed: Aug. 4, 2006

(65) Prior Publication Data

US 2008/0030736 A1    Feb. 7, 2008

(51) Int. Cl.
*G01N 21/55* (2006.01)

(52) U.S. Cl. .................... 356/445; 356/446; 435/287.1; 435/287.7; 435/288.7

(58) Field of Classification Search ................ 356/445, 356/446; 435/287.1–287.7, 288.7
See application file for complete search history.

(56) References Cited

U.S. PATENT DOCUMENTS

| | | | | |
|---|---|---|---|---|
| 5,266,803 | A | * | 11/1993 | Heffelfinger ................ 250/582 |
| 6,697,158 | B2 | * | 2/2004 | Ogura et al. ................ 356/445 |
| 6,714,303 | B2 | * | 3/2004 | Ivarsson .................... 356/445 |

OTHER PUBLICATIONS

Inventor(s): Van Wiggeren et al., Title: "Measurement System Having Modulated Laser Source," filed Aug. 5, 2005, U.S. Appl. No. 11/197,873, Status: Pending.

* cited by examiner

*Primary Examiner*—Gregory J Toatley, Jr.
*Assistant Examiner*—Iyabo S Alli
(74) *Attorney, Agent, or Firm*—Marc Bobys (57) ABSTRACT

The use of a high power and an incoherent light source to reduce noise associated when investigating unknown molecules in Surface Plasmon Resonance (SPR) systems. High power and incoherent light sources can improve resolution and accuracy of SPR system measurements.

16 Claims, 10 Drawing Sheets

OPTICAL SOURCES FOR SPR APPLICATIONS

BACKGROUND OF THE INVENTION

Surface Plasmon Resonance (SPR) is a physical phenomenon that is commonly used to investigate the binding properties of chemical and biological molecules. Analytes may bind to immobilized probe molecules on a metal film, altering a resonance characteristic of the surface plasmon and changing the refractive index around the metal film. SPR systems can detect such changes in refractive index. These changes can be measured as an angle shift or alternatively, as a wavelength shift.

Figure 1:
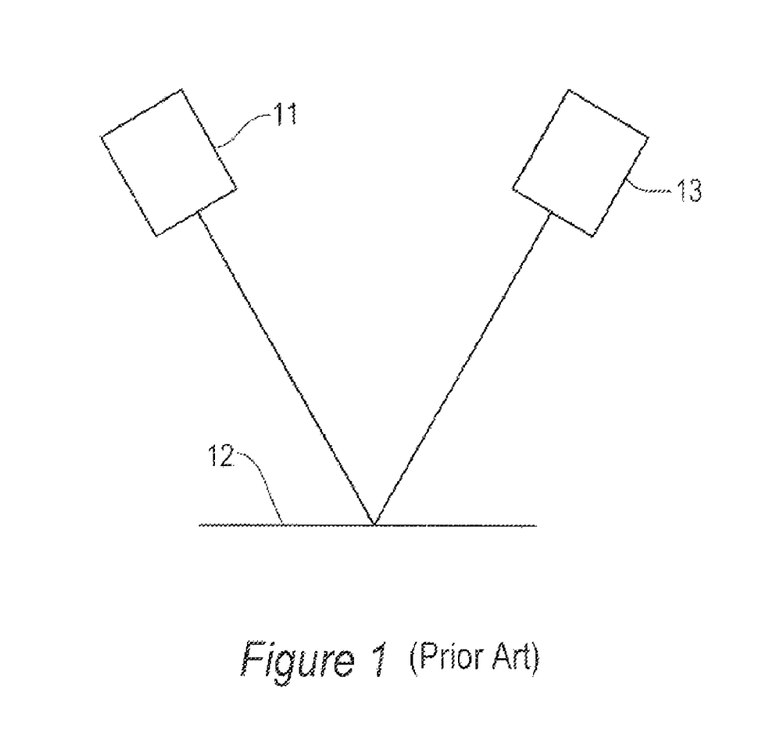
FIG. 1 shows a conventional SPR measurement system of the prior art.

FIG. 1 shows a SPR measurement system. A light source 11 projects a beam of light onto a target 12. The light is reflected off the target onto a photo detector 13.

Some SPR systems use incoherent sources such as Light Emitting Diodes (LEDs). The LED can give adequate performance under some conditions, but its broad spectrum of incoherent light poses a Signal to Noise Ratio (SNR) problem that makes it unsuitable when high resolution and accuracy are needed.

Resolution and accuracy of measurement results can be improved moderately by increasing the power of an incoherent light source in a SPR system. As optical power increases, SNR of the measured signal at photo detector 13 improves. Unfortunately, this approach does not fully solve the problem because LEDs provide limited power density due to their inherent design.

To overcome this limitation, a laser can be used in place of a LED. A laser can provide the optical power density necessary to facilitate tests with better resolution. A laser under normal operating conditions, i.e. when driven well above the threshold, produces high power and coherent light. But under these normal operating conditions, high power coherent light sources introduce optical interference that leads to distorted measurements because of random shifts in standing wave patterns. These shifts in the standing wave patterns degrade the ability of an SPR measurement system to resolve minute changes in the refractive index and, therefore, limit the ability of the system to measure binding analytes.

There remains a need for a way to improve the resolution and accuracy of SPR systems.

SUMMARY OF THE INVENTION

An optical system according to an embodiment of the invention includes an optical source, a target including a reflective surface and a detector. The optical source generates an incoherent light beam with a source line width of about 0.1 nm to 20 nm. The target receives the light beam and produces reflected light indicative of a change in refractive index at the reflective surface. The detector receives the reflected light. In some embodiments, analytes in a test bed are adsorbed onto the reflective surface.

BRIEF DESCRIPTION OF THE DRAWINGS

FIG. 13A-E illustrates embodiments of an incoherent and high power light source.

DETAILED DESCRIPTION

Figure 3:
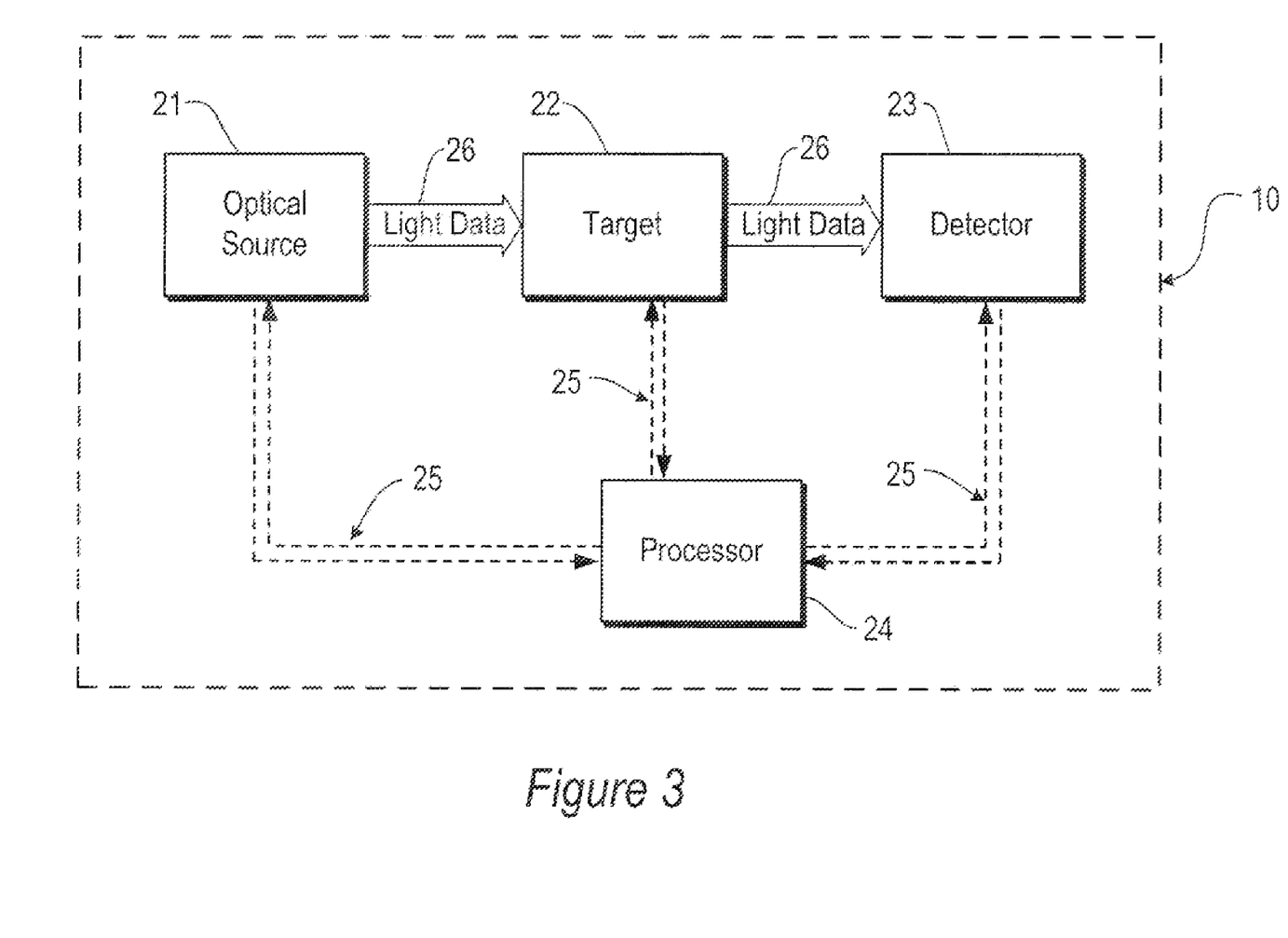
FIG. 3 shows a modular representation of a SPR system according to an embodiment of the present invention.

As shown in FIG. 3, a novel SPR system embodying the invention uses an innovative light source having an incoherent output. The system 10 includes an optical source 21 containing the innovative light source, a target 22 and a detector 23. Light follows an optical path 26 from the optical source 21 to the target 22. Light reflected from the target is captured by the detector 23. In some embodiments, a processor 24 is connected to the optical source, the target and the detector via electrical cables 25, to control the measurement and analysis.

Figure 2:
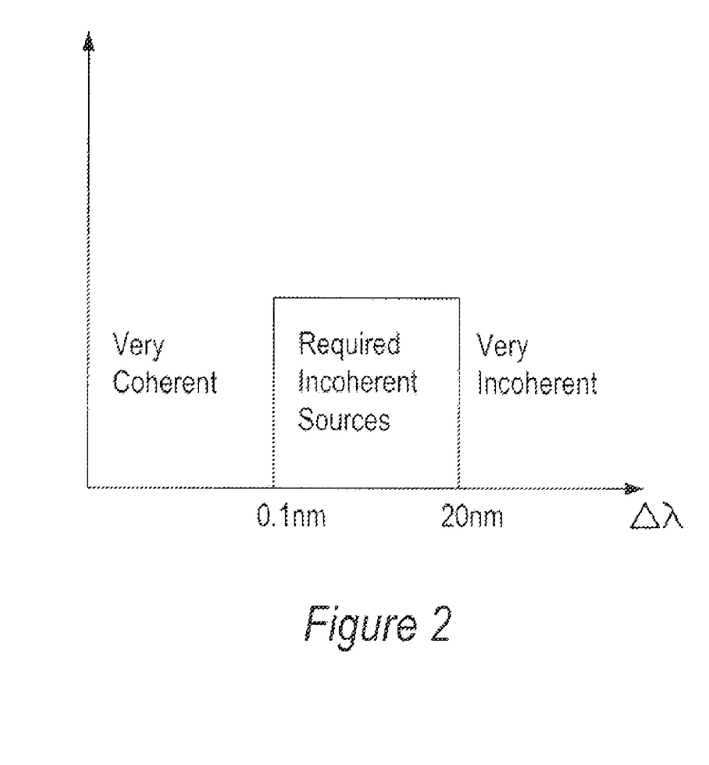
FIG. 2 shows a range of source line widths for high sensitivity SPR sensing.

A range of suitable light source line widths for high sensitivity SPR sensing is approximately 0.1 nm to 20 nm. This is shown in FIG. 2. For an incoherent light source to resolve the resonance dip of typical SPR systems, the spectral width or source line width must be smaller than the spectral width of the SPR resonance. In typical SPR sensing systems, light sources with a source line width greater than 20 nm will be less accurate in resolving the resonance dip and will affect sensitivity. Conversely, a highly coherent light source with a source line width of less than 0.1 nm degrades the system's ability to measure analytes due to noise related to optical interference.

Figure 4:
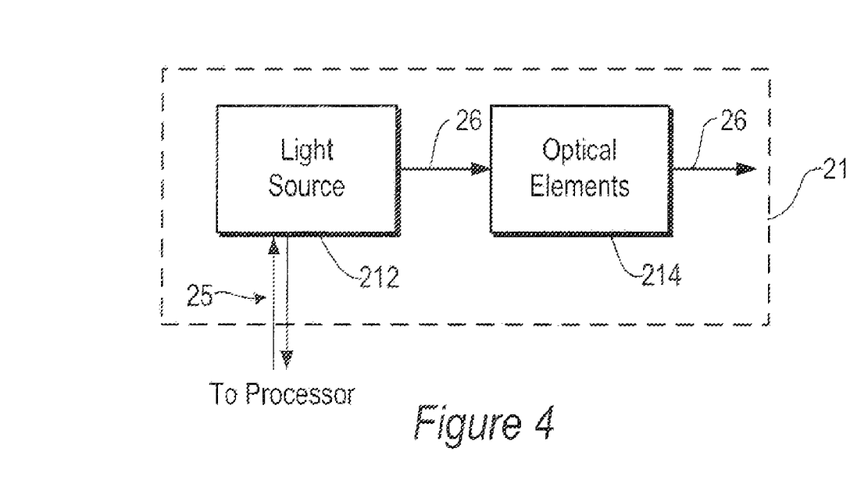
FIG. 4 describes the optical source shown in FIG. 3.

FIG. 4 illustrates the optical source 21 shown in FIG. 3. The optical source consists of the innovative light source 212 and an optional optical element 214 which may be a focusing lens or a set of lenses.

Figure 5:
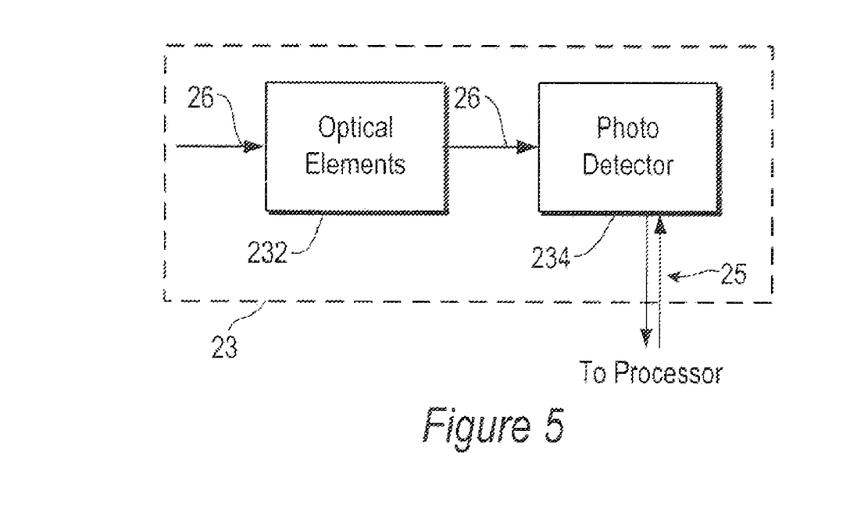
FIG. 5 describes the detector shown in FIG. 3.

FIG. 5 illustrates the detector 23 shown in FIG. 3. The detector 23 includes a photo detector 234 that receives light from the target 22. This light may pass through an optional optical element 232, e.g. a set of imaging lenses as shown.

Figure 6:
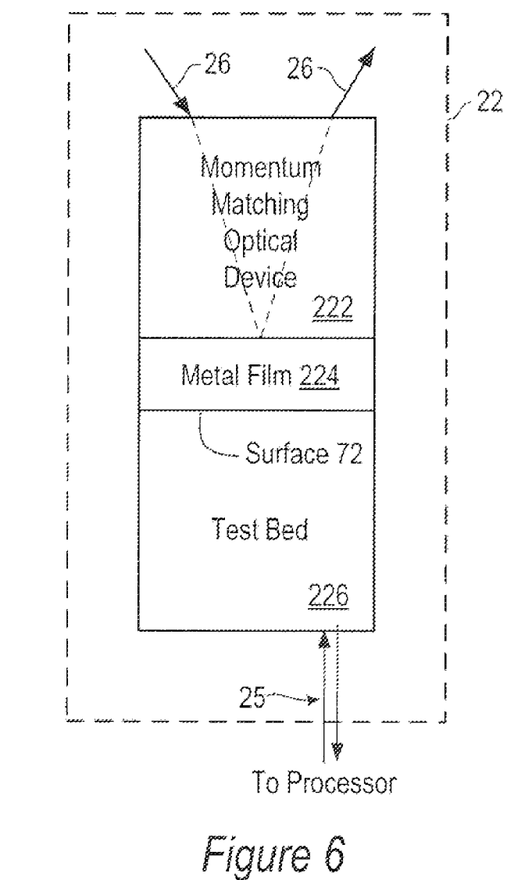
FIG. 6 describes the target shown in FIG. 3.

FIG. 6 illustrates the target 22 shown in FIG. 3. The target may comprise a momentum matching optical device 222, a metal film 224 and a test bed 226. In this embodiment, the metal film is adhered to a surface of the momentum matching optical device. In other embodiments, the metal film, in the form of a metal grating, can emulate the function of the momentum matching device. The test bed facilitates the flow of analytes and is placed below the surface of the momentum matching device and the metal film.

Figure 7:
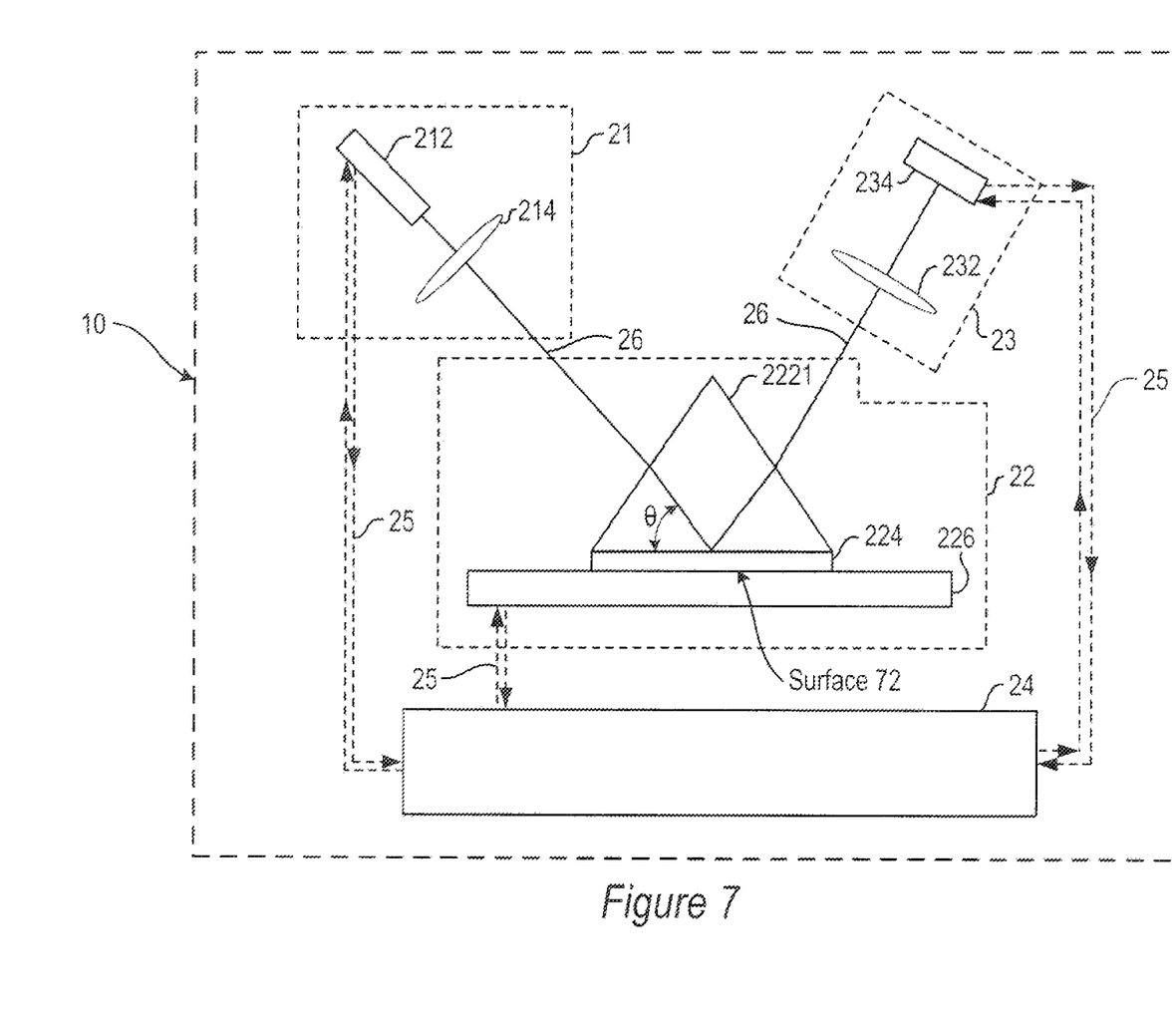
FIG. 7 illustrates in detail an embodiment of the SPR system shown in FIG. 3.

FIG. 7 shows in detail the various components that make up the first embodiment of the SPR system 10. The innovative light source 212 with a high power incoherent output is focused upon a momentum matching optical device 222 through an optional focusing lens 214. A three sided transparent prism 2221, made of glass or plastic, is shown as an embodiment of a momentum matching optical device.

Figure 8:
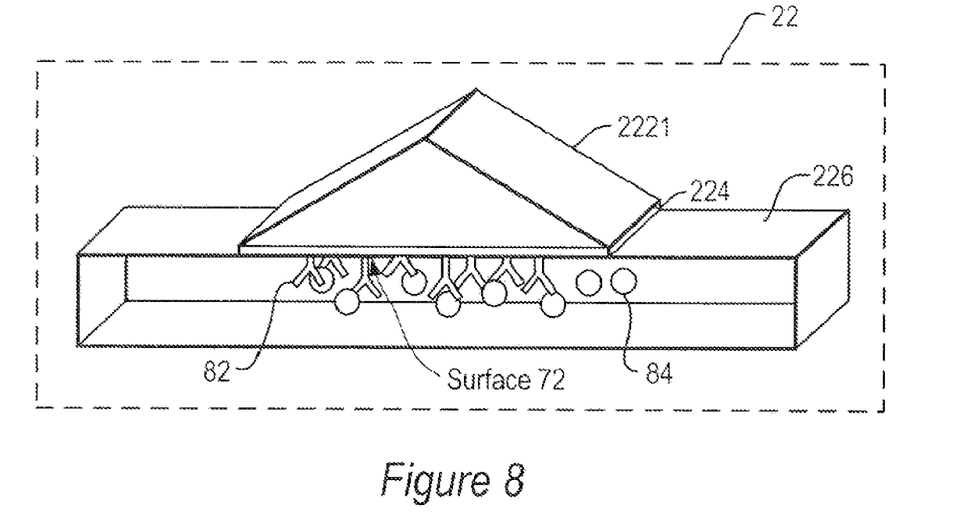
FIG. 8 illustrates a metal film and immobilized probes.

Metal film 224, e.g. gold, silver or aluminum, is coated to a surface of the prism 2221. FIG. 8 shows immobilized probes 82 chemically bound to the metal film. These immobilized probes, or molecules of matching specificity (to the analytes), trigger the binding of analytes 84 to the metal film.

The analytes 84, or molecules under test, are exposed to the metal film 224, e.g. through a cavity in the test bed 226 that allows the analytes to bind with immobilized probes 82. The test bed regulates the flow of the analytes, e.g. by a motorized pump (not shown).

Referring to FIG. 7, the light source 212 is aimed through optional focusing lens 214 at the metal film 224 at an angle θ, referred to as the angle of incidence.

As analytes 84 bind to the immobilized probes 82 on the metal film 224, the refractive index of surface 72 changes. The refractive index of this surface determines the amount of light absorbed or alternatively reflected onwards.

Figure 9:
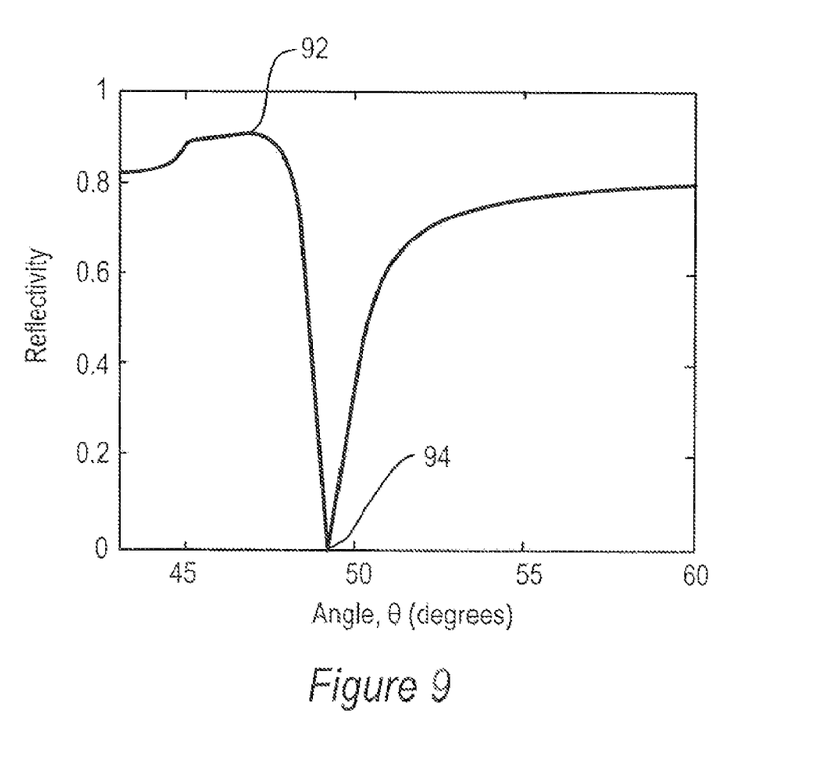
FIG. 9 is a graph of a SPR measurement done by angle shift approach.

FIG. 9 is a graph of an SPR measurement using the angle shift method. The angle of incidence is varied to determine a high level of reflectance 92 and then minimum reflectance 94; the latter also referred to as "reflectance minima" or "surface plasmon resonance angle". At reflectance minima, incident light is most strongly absorbed at surface 72 or correspondingly the least amount of light reflected onwards. As the angle of incidence is increased from reflectance minima, light absorption at surface 72 decreases and correspondingly intensity of reflected light off surface 72 increases.

The binding of analytes 84 changes the refractive index around the metal film creating a change in surface plasmon resonance angle. In the angle shift method the changes in surface plasmon resonance angle are measured to determine the binding characteristics of the analytes.

In other embodiments, dielectric materials can be used with the metal film 224 to increase sensitivity of binding analytes at the metal surface.

Throughout the process described above, light reflected out prism 2221 is collected through an optional imaging lens 232 and onward into a photo detector 234.

The processor 24 may control the light source 212, the test bed 226 and the collection of data from the photo detector 234.

The optical power of the reflected light is measured at the photo detector 234 and the processor 24 records a value for the optical power received.

Figure 10:
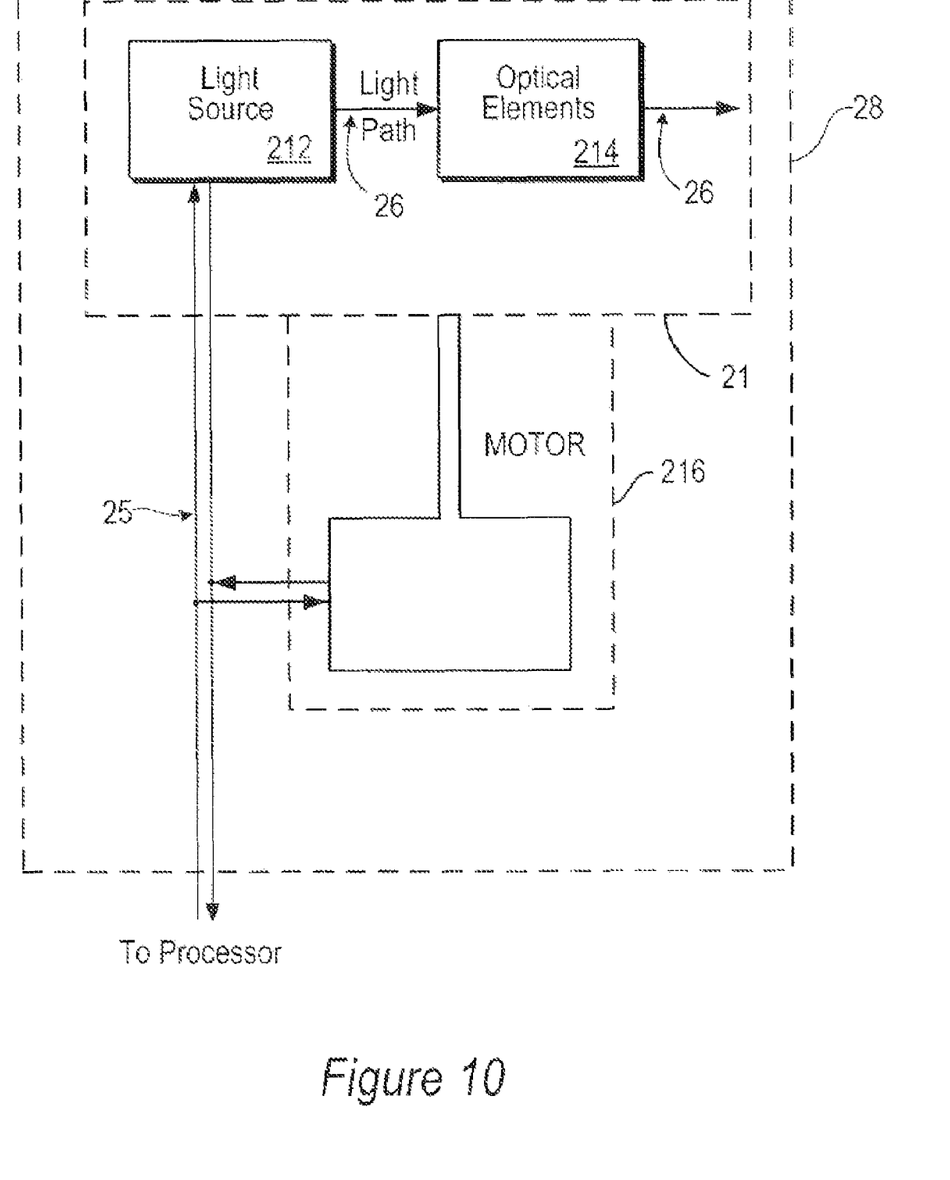
FIG. 10 shows a modular representation of the optical source and a motor.

FIG. 10 illustrates a modular diagram 28 where the optical source 21 is connected to a motor 216 that moves the optical source to mechanically alter the angle of incidence.

Figure 11:
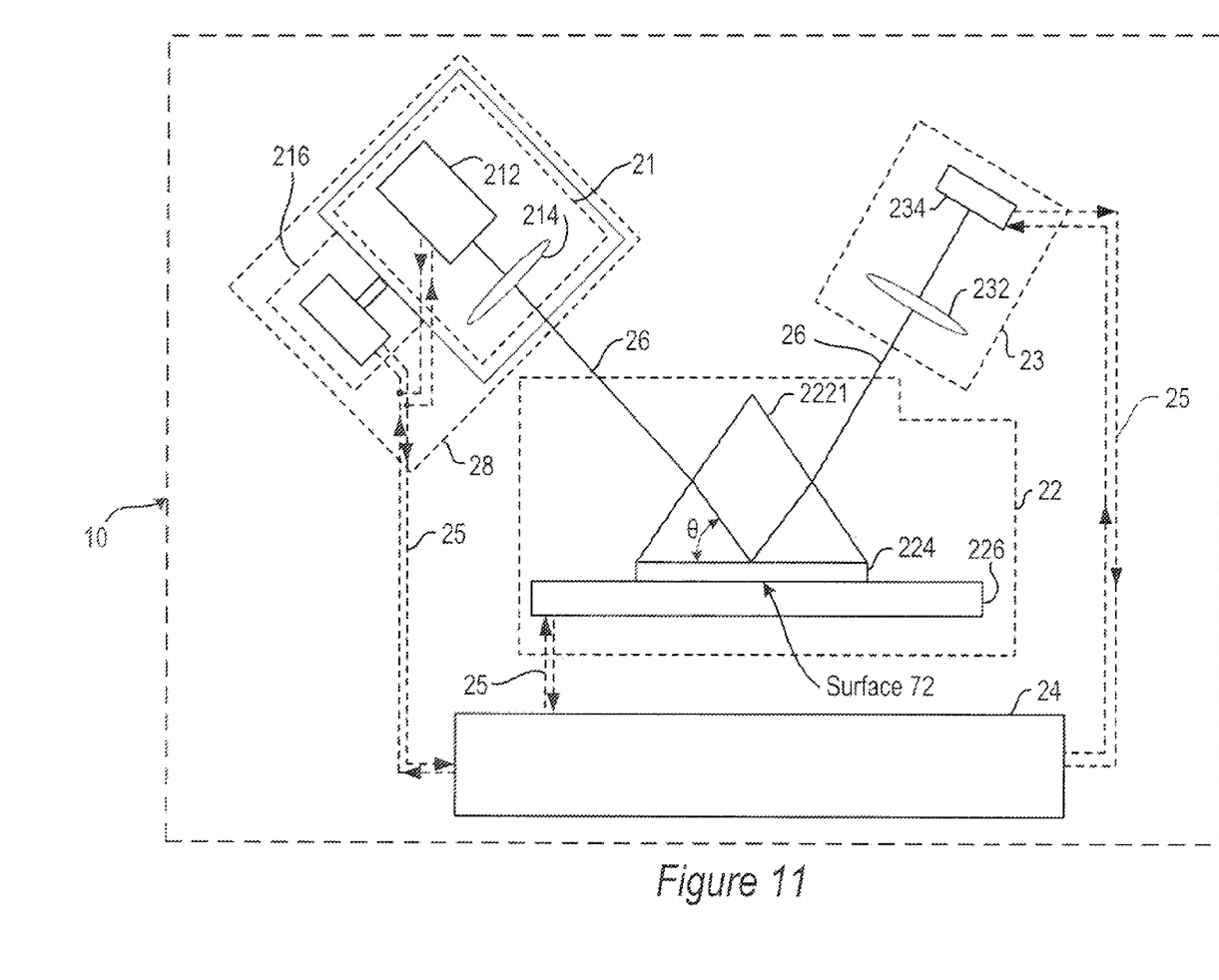
FIG. 11 illustrates in detail the SPR system shown in FIG. 10.

FIG. 11 illustrates in detail this modular diagram described above as a second embodiment of the SPR system 10. The processor 24 controls the motor 216, which in turn mechanically alters the angle of incidence of the light source 212. As described earlier, the processor controls the test bed 226, which in turn regulates the flow of the analytes. Similarly, the optical power of the reflected light is measured at the photo detector 234 and the processor records a value for the optical power received corresponding to an angle of incidence at the light source.

Figure 12:
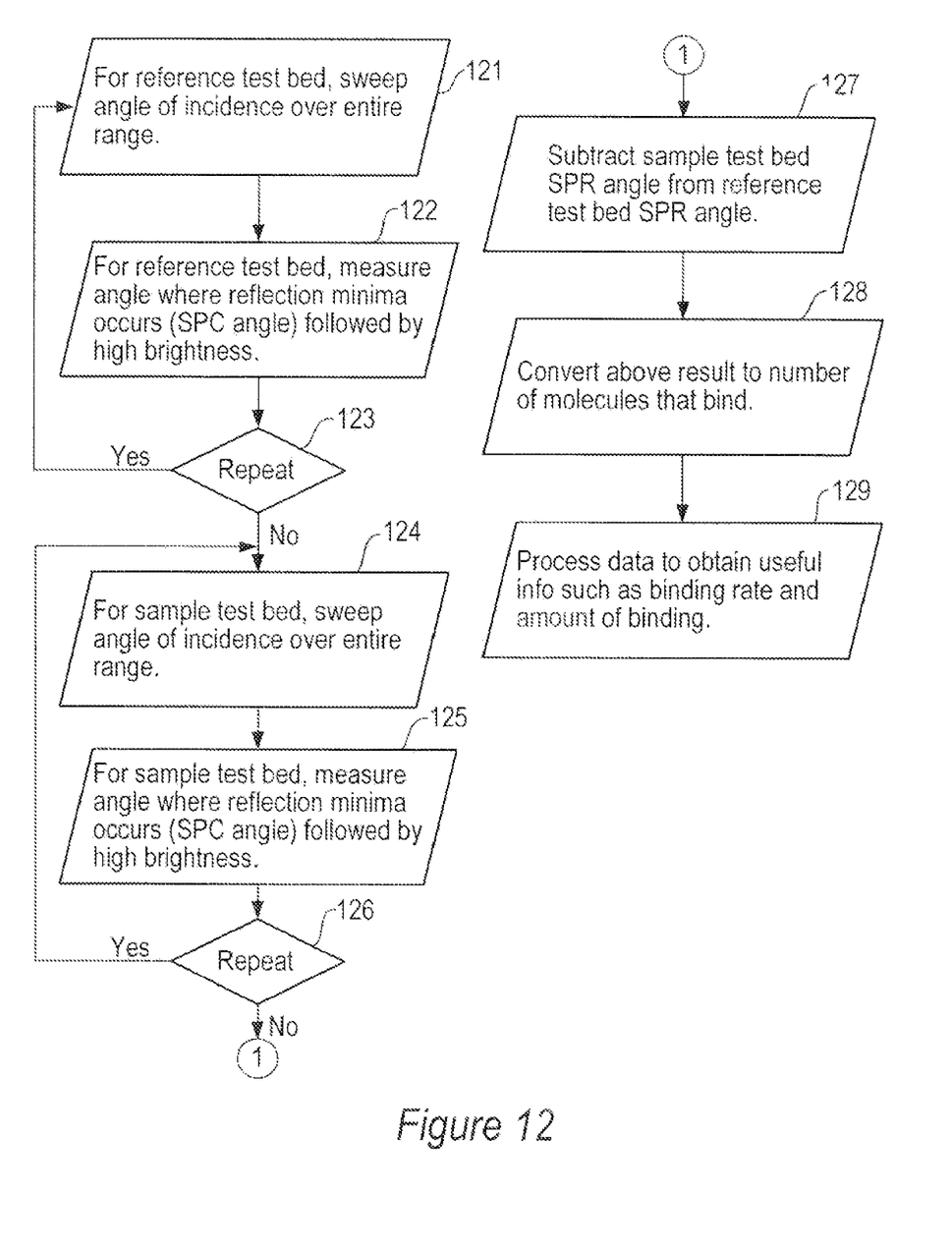
FIG. 12 shows a flow chart of the measurement process of a SPR system.

FIG. 12 details the measurement process in a flow chart. Measurements may begin with the reference test bed by sweeping the angle of incident light over the target block to identify a high level of reflectance or brightness (Block 121). The flow within the test bed is regulated to facilitate the movement of analytes and subsequently the adsorption rate of analytes to immobile probes. As the angle of incidence is altered, the surface plasmon resonance angle is continuously monitored by observing the reflectance minima followed by a high level of brightness (Block 122 and 123). Tests are then repeated for a sample test bed. Blocks 124, 125 and 126 correspond to Blocks 121, 122 and 123 for the respective sample and reference test bed processes. The sample and reference surface plasmon resonance angles are compared i.e. subtracted to eliminated common mode effects (Block 127).

In this manner, information about the binding characteristics of the analytes is determined, e.g. amount and rate of binding (Block 128 and 129). This measurement procedure is one example of an angle shift method used in SPR sensing. FIG. 9 illustrates results derived from an angle shift method.

The flow described above can be done by an individual manually or with the aid of software and the processor in an automated setting.

In a third embodiment of a SPR system, the processor 24 alters the wavelength of a wavelength-tunable light source and measures the corresponding intensity at the photo detector 234. An intensity minimum will occur when the wavelength of the incident light equals the surface plasmon resonance wavelength. In a manner analogous to the angle shift method described above, changes in the surface plasmon resonance wavelength are monitored and correlated with the binding of molecules to the immobilized probes.

Amplified Spontaneous Emission (ASE) devices are examples of embodiments of the innovative light source 212. ASEs devices are used to create incoherent radiation at high brightness. ASE is caused by spontaneous emission that becomes amplified through stimulated emissions. Examples of ASE devices are LEDs that are specially designed so that a large portion of the emitted light is produced by the phenomenon of ASE. Other examples are Superluminescent LEDs (SLED), pumped fiber and solid state sources. ASE devices can also be used with an optical power amplifier-filter as examples of the innovative light source.

An optical power amplifier-filter is a combination of an optical spectral filter and an optical power amplifier. An optical spectral filter narrows the spectral width of the source to within 0.1 nm to 20 nm. An optical power amplifier magnifies the output power. The optical power amplifier-filter may also be placed anywhere in the light path between optical source 21 and the detector 23 as long as the optical system behaves linearly with respect to the optical field.

Examples of other sources that can be used in conjunction with an optical power amplifier-filter as embodiments for the innovative light source 212 are light bulbs, fluorescent tubes and off-the-shelf LEDs.

Figure 13:
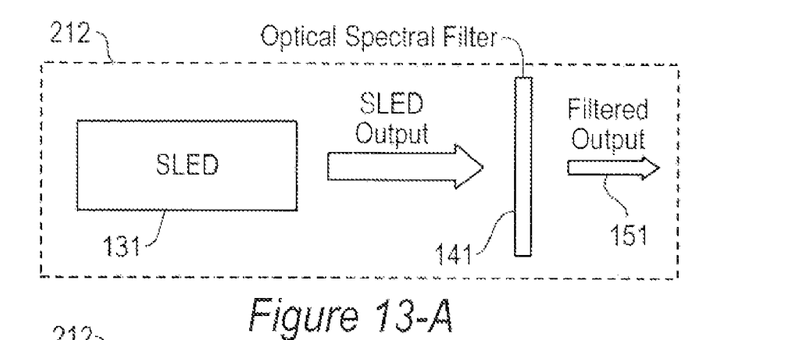

FIG. 13-A illustrates a SLED 131 with an optical spectral filter 141 as an embodiment of the innovative light source 212. The SLED has a very high incoherency property and falls outside the required line width but a suitable optical output power. When used in conjunction with an optical spectral filter to narrow the spectral width, the resulting filtered output 151 has its line width within 0.1 nm to 20 nm. The optical power may be attenuated by the filter but still suitable for this application.

In FIG. 13-B a SLED 132 has desirable incoherency output characteristics but insufficient optical power. It is used in conjunction with a semiconductor optical amplifier (SOA) 142 to produce a suitable optical power. The resulting output 152 meets the requirements of the innovative light source 212.

FIG. 13-C combines the embodiments shown in FIG. 13-A and FIG. 13-B. A SLED 133 with a low power output as well as very high incoherency property is used in conjunction with an optical spectral filter 141 and a SOA 142. The resultant output 153 meets the desired line width and optical power requirements.

In another embodiment of an innovative light source 212, FIG. 13-D illustrates a fiber Bragg grating 510, Erbium doped fiber 520, pumped fiber light source 540 and a coupler 530. The fiber Bragg grating, a set of spectrally selective mirrors, performs the optical spectral filtering function. The pumped fiber light source is coupled into the Erbium doped fiber cable through a coupler region. The coupled output is amplified by the Erbium doped cable and reflected off the fiber Bragg grating to confine the line width and output power to within the range desired.

Yet another embodiment of an innovative light source 212, FIG. 13-E incorporates a fiber Bragg grating 512 into the internal structure of a SLED 134. In this embodiment, a waveguide 610 acts as an internal conduit for the light output and is amplified by an optical gain region 620 and spectrally filtered by the fiber Bragg grating 512.

The invention claimed is:

1. An optical system comprising:
an optical source capable of generating a light beam with a source line width of about 0.1 nm to 20 nm;
a target including a reflective surface, capable of receiving the light beam at an angle of incidence and producing reflected light indicative of a change in refractive index at the reflective surface; and
a detector capable of receiving the reflected light and producing a signal indicative of the reflected light.

2. An optical system of claim 1 and further comprising a test bed adjacent to the reflective surface and capable of affecting the change in refractive index.

3. An optical system of claim 2 and further comprising analytes flowing in the test bed whereby the analytes are adsorbed to the reflective surface.

4. An optical system of claim 3 and further comprising a processor to control the optical source, analyze the signal and control the test bed.

5. An optical system of claim 4 and further comprising a motor controlled by the processor and operative to move the optical source and thereby change the angle of incidence.

6. An optical system of claim 1 wherein the optical source comprises a first focusing lens.

7. An optical system of claim 1 wherein the reflective surface consists of a momentum matching optical device and a metal film.

8. An optical system of claim 1 wherein the detector includes a second focusing lens and a photo detector.

9. An optical system of claim 1 wherein the optical source, the target and the detector form a Surface Plasmon Resonance system.

10. An optical system of claim 1 and wherein the optical source comprises an optical power amplifier-filter selected from the group consisting of:
an optical spectral filter;
an optical power amplifier; and
an optical spectral filter and an optical power amplifier.

11. An optical system of claim 1 wherein the optical source is selected from the group consisting of:
an Amplified Spontaneous Emission (ASE) device;
a light bulb;
a fluorescent tube; and
an LED.

12. An optical system of claim 11 wherein the ASE device is selected from the group consisting of:
a Superluminescent Light Emitting Diode (SLED);
a SLED with an integrated grating;
a pumped fiber; and
a solid state source.

13. An optical system comprising:
an optical source capable of generating a light beam;
a target including a reflective surface, capable of receiving the light beam at an angle of incidence and producing reflected light indicative of a change in refractive index at the reflective surface;
a detector capable of receiving the reflected light and producing a signal indicative of the reflected light; and
an optical power amplifier-filter in the path of the light beam modifying the light beam to have a line width of about 0.1 nm to 20 nm.

14. An optical system of claim 13 and wherein the optical power amplifier-filter selected from the group consisting of:
an optical spectral filter;
an optical power amplifier; and
an optical spectral filter and an optical power amplifier.

15. An optical system comprising:
an optical source capable of generating a light beam;
a target including a reflective surface, capable of receiving the light beam at an angle of incidence and producing reflected light indicative of a change in refractive index at the reflective surface;
a detector capable of receiving the reflected light and producing a signal indicative of the reflected light; and
an optical power amplifier-filter in the path of the reflected light modifying the reflected light to have a line width of about 0.1 nm to 20 nm.

16. An optical system of claim 15 and wherein the optical power amplifier-filter selected from the group consisting of:
an optical spectral filter;
an optical power amplifier; and
an optical spectral filter and an optical power amplifier.

* * * * *